US007067134B1

(12) United States Patent
Kang et al.

(10) Patent No.: US 7,067,134 B1
(45) Date of Patent: Jun. 27, 2006

(54) HIV VACCINE

(75) Inventors: Chil-Yong Kang, London (CA); Yan Li, London (CA)

(73) Assignee: University of Western Ontario, London (CA)

( * ) Notice: Subject to any disclaimer, the term of this patent is extended or adjusted under 35 U.S.C. 154(b) by 0 days.

(21) Appl. No.: 09/762,294

(22) PCT Filed: Aug. 12, 1999

(86) PCT No.: PCT/CA99/00746

§ 371 (c)(1),
(2), (4) Date: Apr. 2, 2001

(87) PCT Pub. No.: WO00/09703

PCT Pub. Date: Feb. 24, 2000

Related U.S. Application Data

(60) Provisional application No. 60/096,235, filed on Aug. 12, 1998.

(51) Int. Cl.
*A61K 39/21* (2006.01)
(52) U.S. Cl. ............................... 424/188.1; 424/208.1; 435/236
(58) Field of Classification Search ............. 424/188.1, 424/208.1, 192.1; 435/236
See application file for complete search history.

(56) References Cited

FOREIGN PATENT DOCUMENTS

WO      WO 9417825      8/1994

OTHER PUBLICATIONS

Haynes, B. F., et al., 1996, "Update on the issues of HIV vaccine development", Ann. Med. 28:39-41.*
Haynes, B. F., 1996, "HIV vaccines: where are we and where are we going?", Lancet 348:933-37.*
Burton, D. R., and J. P. Moore, 1998, "Why do we not have an HIV vaccine and how can we make one?", Nat. Med. Vac. Suppl. 4(5):495-98.*
Letvin, N. L., 1998, "Progess in the development of an HIV-1 vaccine", Science 280:1875-1880.*
Lee, T.-H., 1997, "Acquired immunodeficiency disease vaccines: design and development", in AIDS: Biology, Diagnosis, Treatment, and Prevention, fourth edition, DeVita, Jr., V. T., et al., eds., Lippincott-Raven Publishers, pp. 605-616.*

Stevenson, M., et al., 1988, "Envelope glycoprotein of HIV induces interference and cytolysis resistance in CD4+ cells: mechanism for persistence in AIDS", Cell 53(3):483-496 (abstract provided).*
Siliciano, R. F., et al., 1988, "Analysis of host-virus interactions in AIDS with anti-gp120 T cell clones: effect of HIV sequence variation and mechanism for CD4+ cell depletion", Cell 54(4):561-575 (abstract provided).*
Weinhold, K., et al., 1989, "HIV-1 gp120-mediated immune suppression and lymphocyte destruction in the absence of viral infection", J. Immunol. 142(9):3091-3097 (abstract provided).*
Jassoy, C., et al., 1993, "Human immunodeficiency virus type 1-specific cytotoxic T lymphocytes . . . ", J. Virol. 67(5):2844-2852.*
Banda, N. K., et al., 1992, "Crosslinking CD4 by human immunodeficiency virus gp120 primes T cells for activation-induced apoptosis", J. Exp. Med. 176(4):1099-1106 (abstract provided).*
Laurent-Crawford, A. G., et al., 1993, "Membrane expression of HIV envelope glycoproteins triggers apoptosis in CD4 cells", AIDS Res. Human Retrovir. 9(8):761-773 (abstract provided).*
Li, Y., et al., 1994, "Control of expression, glycosylation, and secretion of HIV-1 gp120 by homologous and heterologous signa sequences", Virol. 204:266-278.*
Li, Y., et al., 1996, "Effects of inefficient cleavage of the signal sequence of HIV-1 gp120 on its asociation with calnexin, folding and intracellular transport", Proc. Natl. Acad. Sci. USA 93:9606-9611.*
Daniel, M. D., et al., 1992, "Protective effects of a live attenuated SIV vaccine with a deletion in the nef gene", Science 258(5090):1938-41 (abstract provided).*
Chakrabarti et al., Proceedings of the National Academy of Sciences of USA, vol. 93, No. 18, p. 9810-9815 (1996).
Li et al., Proceedings of the National Academy of Sciences of USA, vol. 93, No. 18, p. 9606-9611 (1996).
Li et al., Virology, vol. 204, No. 1, p. 266-278 (1994).

* cited by examiner

*Primary Examiner*—Jeffrey S. Parkin
(74) *Attorney, Agent, or Firm*—Jennifer A. Zarutskie; Foley Hoag LLP

(57) ABSTRACT

A novel HIV vaccine is provided. In particular, the vaccine comprises an avirulent and non-cytolytic recombinant HIV wherein the NSS of the virus' envelope glycoprotein is replaced with a non-cytolytic signal sequence and nef gene of the virus is deleted which renders the virus avirulent.

13 Claims, 12 Drawing Sheets

HIV VACCINE

FIELD OF THE INVENTION

The invention relates to a novel vaccine for use in treatment of AIDS as well as methods for production thereof. More particularly the invention relates to a vaccine which may be produced in large quantities and which is non-cytolytic and avirulent.

BACKGROUND OF THE INVENTION

Despite recent advances in antiviral therapy, there is no permanent cure for AIDS or HIV infection. Drug therapy, is a promising arena of investigation in terms of providing effective therapy, however because of side effects, compliance, and expense, progress has not been rapid. Compounding these difficulties is the fact that the availability of such drugs is limited in developing countries where it is estimated that 90% of HIV infections will occur by the year 2000.

Due to the success that vaccines to infectious diseases have had, the most noteable being against small pox and polio, the search for an effective vaccine against AIDS continues. A variety of approaches have been tried. Indeed, most HIV-1 vaccine development has concentrated on subunit vaccines. The difficulty with the subunit vaccine approach has been the ability to produce optimal immunity. At present, it is not known exactly which components of the HIV antigen(s) and the immune system are necessary for protection from natural infection.

Early vaccine trials have looked at recombinant subunit protein based immunogens, such as the HIV-1 envelope protein gp120. The results from this approach have been disappointing, although, immunization regimens that employ both live recombinant virus and subunit protein have, in some individuals, elicited both envelope specific CD8+ CTL and neutralizing antibody to the HIV-1 envelope (Cooney E L, et al., Proc Natl Acad Sci USA 1993; 90; 1882–86; McElrath M J, et al. J Infect Dis. 169: 41–47 (1994); Graham B S, et al. J Infect Dis 166: 244–52 (1992); and Graham B S, et al. J Infect Dis 167: 533–37 (1993)).

Studies of the envelop glycoprotein of HIV have not yielded a plausible path to vaccine development. For example, in respect of HIV-1 gp120, the signal sequence of HIV-1 envelop glycoprotein gp120, which is referred to as NSS for HIV-1 natural signal sequence, has been found to be associated with the extent of secretion of gp120. In this respect it has been shown that substitution of the NSS with either mellitin or IL-3 signal sequence renders a high level production and efficient secretion of gp120 (Li, Y., et al. Virology 204: 266–278 (1994); and Li, Y., et al. Proc. Natl. Acad. Sci 0.93: 9606–9611 (1996). However, it is not known whether the signal sequence of HIV-1 gp120 has a role to play in the pathogenicity of the virus.

The preferred route is the use of whole, inactivated virus vaccines, such as inactivated polio virus vaccine, or attenuated live virus vaccines, such as oral polio vaccine. Unfortunately, this approach in the search for an AIDS virus vaccine appears too dangerous, given the potential for problems such as the "Cutter incident" in which inadequate inactivation of the polio vaccine resulted in actual clinical polio. A previous approach has incorporated use of the wild-type HIV-1, however, it was impossible to produce an adequate amount of virus for killed whole virus because the yield of HIV-1 infected T-cell lines was very low (Coffin et al. Retroviruses, CSH Press, 1989). Assuming it is possible to increase yield, there is also concern about the potential liability in growing large volumes of infectious HIV-1.

With respect to HIV vaccines it is known that deletion of the HIV nef gene attenuates the virus. Desrosiers and his associates have demonstrated that vaccination of macaques with nef-deleted SIV protected wild-type SIV challenge (Daniels, M. D. et al. Science 258:1938 (1992); Desrosiers, R. C., et al. Proc. Natl. Acad. Sci. USA 86:6353 (1989)) and others have demonstrated that nef gene is dispensable for SIV and HIV replication (Daniels, M. D. et al. Science 258:1938 (1992); Gibbs, J. S., et al. AIDS Res. and Human Retroviruses 10:343 (1994); Igarashi, T., et al. J. Gen. Virol. 78:985 (1997); Kestler III, H. W., et al. Cell 65:651 (1991)). Furthermore, deletion of nef gene renders the virus to be non-pathogenic in the normally susceptible host (Daniels, M. D. e t al. Science 258:1938 (1992)). Although this deletion does not provide a form of the virus which is possible to produce in large quantities. Neither too, has this form of the virus been shown to be safe for the production of a vaccine.

Consequently, what is needed is a vaccine which is avirulent as well as being capable of being produced in large quantities, and without the previous concerns and problems of using wild-type HIV-1.

SUMMARY OF THE INVENTION

The present inventors have found that the natural signal sequence (NSS) of the Human Immunodeficiency Virus-1 (HIV-1) envelope glycoprotein gp120 is responsible for apoptosis as well as general necrosis of virus infected cells. The inventors have also found that replacement of the NSS with a more efficient signal sequence, such as mellitin or IL-3 signal sequence, generates a non-cytolytic HIV-1 which is capable of highly efficient replication and secretion of gp120. Consequently, the present invention relates to a non-cytolytic retrovirus which is capable of highly efficient viral replication and which is therefore useful in preparing a retroviral vaccine. In its broadest aspect, the present invention provides an essentially non-cytolytic retrovirus wherein the natural signal sequence of the virus' envelope glycoprotein is modified to be essentially non-cytolytic or is replaced with an essentially non-cytolytic signal sequence.

According to one embodiment, modification of the natural signal sequence of a retrovirus' envelope glycoprotein results in a more efficient replication of the virus, preferably HIV. Accordingly, the present invention provides an essentially non-cytolytic recombinant HIV-1 capable of highly efficient replication wherein the NSS of the virus' envelope glycoprotein is modified sufficiently to prevent cell damage by the virus, preferably by eliminating positively charged amino acids, even more preferably, such elimination or modification resulting in no more than one (1) and preferably zero (0) positively charged amino acids.

In another embodiment, replacement of the natural signal sequence results in a more efficient replication of HIV. Accordingly the present invention provides an essentially non-cytolytic recombinant HIV-1 capable of highly efficient replication wherein the NSS of the virus' envelope glycoprotein is replaced with an essentially non-cytolytic and more efficient signal sequence, preferably containing no more than one and preferably zero positively charged amino acids, more preferably mellitin signal sequence (MSS) or IL-3 signal sequence (ILSS).

According to another embodiment, an essentially non-cytolytic retrovirus is also avirulent. Accordingly, the present invention provides an avirulent, essentially non-cytolytic retrovirus comprising a nucleic acid sequence addition or deletion that renders the virus avirulent and wherein the natural signal sequence of the virus' envelope glycoprotein is either modified or replaced to provide an essentially non-cytolytic signal sequence.

In a preferred embodiment there is provided an avirulent, essentially non-cytolytic, retrovirus which contains a sufficient deletion of nef gene to render the virus non-pathogenic, and wherein the NSS of the virus' envelope glycoprotein gp120 is modified or replaced to provide a more efficient signal sequence.

According to a specific embodiment of the invention there is provided an avirulent, essentially non-cytolytic, HIV-1 capable of highly efficient replication, with sufficient deletion of nef gene to render the virus non-pathogenic in a normally susceptible host and wherein the NSS of the virus' envelop glycoprotein gp120 is replaced with a more efficient signal sequence, preferably MSS or ILSS.

In another aspect, the present invention provides a vaccine against a retroviral infection comprising an essentially non-cytolytic recombinant retrovirus wherein the NSS of the virus' envelope glycoprotein is modified to provide an essentially non-cytolytic NSS or is replaced with an essentially non-cytolytic NSS. The recombinant retrovirus can provide protection to the wild type retrovirus notwithstanding the genetic modifications incorporated into the recombinant retrovirus, as it will contain the necessary conformational epitopes to generate protective immunity. Preferably, the retrovirus is HIV, more preferably all different clades of HIV-1.

The present invention also includes a method of preventing apoptosis induced by retroviral infection comprising administering a sufficient amount of antagonist to NSS to an animal in need thereof, preferably an antibody or antisense molecule.

The present invention also includes a method of preventing or treating a retroviral infection comprising administering an essentially non-cytolytic recombinant retrovirus, wherein the NSS of the virus' envelope glycoprotein is modified to provide an essentially non-cytolytic NSS or is replaced with an essentially non-cytolytic NSS, to an animal in need thereof.

The present invention further includes a method of destroying cells referred to herein as "target" cells, preferably cancer cells, comprising administering a recombinant virus, specific for the target cells, which has been engineered to contain the NSS of HIV-1, to an animal in need thereof.

The present invention further includes a cell transfected with a recombinant retrovirus of the present invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Recombinant Retrovirus

Figure 1:
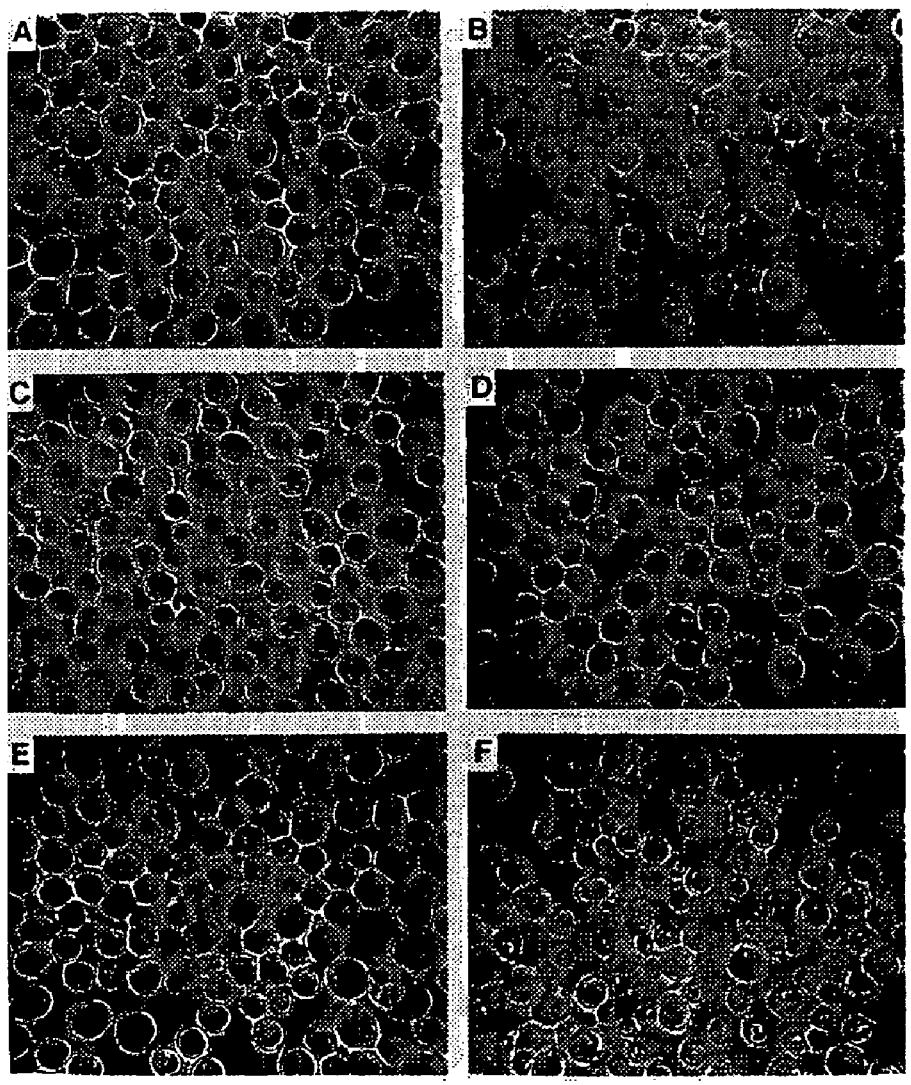
FIG. 1 is photographs of microscopic examination of recombinant baculovirus (AcNPV) infected SF2/insect cells.
Figure 2:
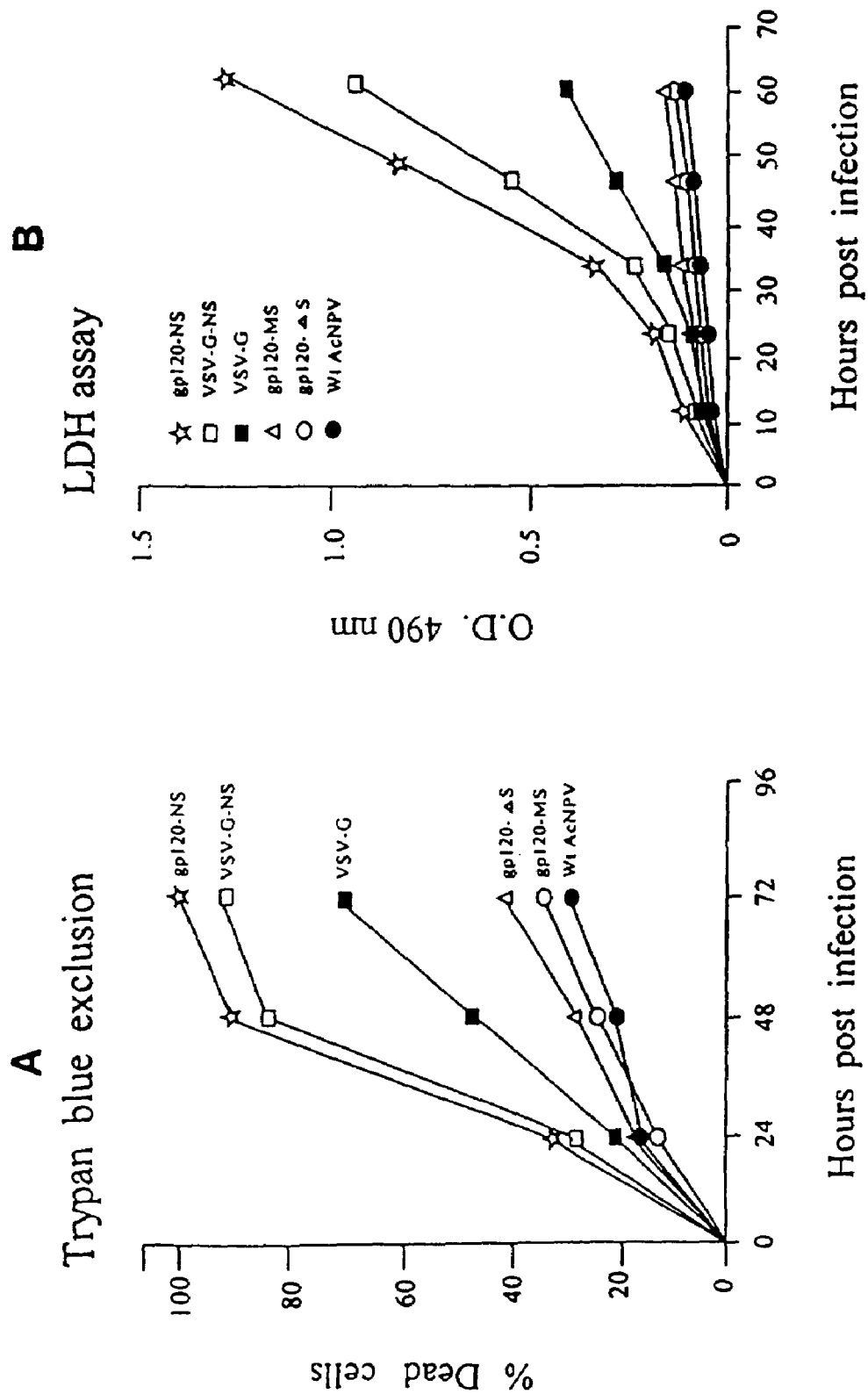
FIG. 2 provides graphs illustrating the effects of HIV-1 env signal sequence on cell death.

As mentioned hereinabove, the present invention relates to an essentially non-cytolytic retrovirus wherein the natural signal sequence of HIV-1 envelope glycoprotein gp120 (NSS) is modified to be essentially non-cytolytic or is replaced with an essentially non-cytolytic signal sequence. The term "essentially non- cytolytic" as used herein means that the retrovirus does not significantly damage or kill the cells it infects.

In one embodiment, the present invention provides an essentially non-cytolytic recombinant HIV-1 capable of highly efficient replication wherein the NSS of the virus' envelope glycoprotein is modified sufficiently to prevent cell damage by the virus, preferably by eliminating positively charged amino acids, even more preferably, such elimination or modification resulting in no more than one (1) and preferably zero (0) positively charged amino acids. The positively charged amino acids which may be modified or replaced include lysine and arginine.

In another embodiment, replacement of the natural signal sequence results in a more efficient replication of HIV. Accordingly the present invention provides an essentially non-cytolytic recombinant HIV-1 capable of highly efficient replication wherein the NSS of the virus' envelope glycoprotein is replaced with an essentially non-cytolytic and more efficient signal sequence. In a preferred embodiment, replacement of the NSS of the envelope glycoprotein of HIV-1 with either the mellitin or IL-3 signal sequence decreases the cytotoxicity of the retrovirus. As such, the present invention includes within its scope replacement of NSS with any signal sequence which renders the retrovirus essentially non-cytolytic. The inventors have also shown that replacement of the NSS with mellitin or IL-3 signal sequences results in a greater level of production and secretion of gp120, in addition to the reduced cytotoxicity. The inventors have also shown that replacement of the NSS results in partial deletion the vpu gene. Studies have shown the vpu gene can be completely deleted without any measurable impact on the virus' ability to replicate (James et al. AIDS Res. Human Retrovirus 10:343–350, 1994).

In another embodiment, the retrovirus is rendered avirulent. In a preferred embodiment, the virus is rendered avirulent by deleting the nef gene. Accordingly, the present invention provides an avirulent, essentially non-cytolytic retrovirus which contains a sufficient deletion of the nef gene to render the virus non-pathogenic and wherein the virus' envelope glycoprotein gp120 coding sequence is replaced with a more efficient signal sequence. As used herein, "sufficient deletion" means deletion of enough of the sequence to prevent transcription and thereby production of the nef protein product.

In a further embodiment, the retrovirus is rendered avirulent, essentially non-cytolytic, and contains a sufficient deletion of the nef gene and the vpu gene to render the virus non-pathogenic.

The recombinant retrovirus of the present invention can be any retrovirus including HIV-1, HIV-2, SIV, HTLV-1. Preferably the retrovirus is a human immunodeficiency virus selected from HIV-1 and HIV-2, more preferably, the retrovirus is HIV-1.

The recombinant retroviruses of the present invention can be prepared using techniques known in the art. In one embodiment, the retrovirus may be introduced in a host cell under conditions suitable for the replication and expression of the retrovirus in the host. Accordingly, the present invention also provides a cell transfected with a recombinant retrovirus wherein the natural signal sequence of the virus' envelope glycoprotein gp120 is modified to provide an essentially non-cytotoxic virus or is replaced with an essentially non-cytolytic signal sequence. The cell is preferably a T-lymphocyte, more preferably a T-cell that is not derived from a transformed cell line.

The essentially non-cytolytic and avirulent retrovirus of the present invention will be extremely useful for the prevention and treatment of a retroviral infection as the retrovirus may be produced in large quantities and in a form that is non-pathogenic to the host, preferably the virus of the invention will be useful for development of HIV/AIDS vaccines for the prevention and treatment of HIV infections. Accordingly, the present invention also provides a method of preventing or treating a retroviral infection comprising administering an effective amount of a killed recombinant essentially non-cytolytic avirulent retrovirus of the present invention to an animal in need thereof. The term "effective amount" as used herein means an amount effective and at dosages and for periods of time necessary to achieve the desired result. The term "animal" as used herein includes all members of the animal kingdom including mammals, preferably humans.

In a preferred embodiment, the present invention provides a method of preventing or treating a retroviral infection comprising administering an effective amount of a killed recombinant essentially non-cytolytic avirulent retrovirus to an animal in need thereof, wherein the natural signal sequence of the virus' envelope glycoprotein, preferably gp120, is modified to provide an essentially non-cytolytic signal sequence, preferably the virus is rendered avirulent by deleting the nef gene. According to a preferred embodiment the modification to provide a non-cytolytic NSS results in no more than one positively charged amino acid in the NSS sequence, more preferably zero positively charged amino acids. Most preferably, the animal is a human, preferably the retrovirus is HIV-1.

In a further preferred embodiment, the present invention provides a method of preventing or treating a retroviral infection comprising administering an effective amount of a killed recombinant essentially non-cytolytic avirulent retrovirus to an animal in need thereof, wherein the natural signal sequence of the virus' envelope glycoprotein, preferably gp120, is replaced with an essentially non-cytolytic signal sequence, preferably the virus is rendered avirulent by deleting the nef gene. Most preferably, the animal is a human, preferably the retrovirus is HIV-1.

According to a preferred embodiment of the method wherein the NSS is replaced, the non-cytolytic signal sequence is selected from the group consisting of the mellitin sequence and the IL-3 signal sequence.

Vaccines

The present invention further includes a vaccine comprising an effective amount of an avirulent and an essentially non-cytolytic retrovirus wherein the natural signal sequence of the virus' envelope glycoprotein, preferably gp120, is replaced with an essentially non-cytolytic signal sequence and the virus is rendered avirulent by deleting a sufficient portion of the nef gene. The retrovirus may also have a portion of the vpu gene deleted as a result of replacement of the NSS. Preferably the essentially non-cytolytic signal sequence is selected from the group consisting of the mellitin sequence and the IL-3 signal sequence.

According to one embodiment, modification of the natural signal sequence of a retrovirus' envelope glycoprotein results in a more efficient replication of the virus, preferably HIV. Accordingly, the present invention provides a non-cytolytic recombinant HIV-1 capable of highly efficient replication wherein the NSS of the virus' envelope glycoprotein is modified sufficiently to prevent cell damage by the virus, preferably by eliminating positively charged amino acids, even more preferably, such elimination or modification resulting in no more than one (1) positively charged amino acid, more preferably no more than zero (0) positively charged amino acids.

In another embodiment, replacement of the non-cytolytic signal sequence results in a more efficient replication of HIV. Accordingly the present invention provides a vaccine comprised of a non-cytolytic recombinant HIV-1 capable of highly efficient replication wherein the NSS of the virus' envelope glycoprotein is replaced with a non-cytolytic and more efficient signal sequence, preferably containing no more than one positive amino acids, preferably mellitin signal sequence (MSS) or IL-3 signal sequence (ILSS).

According to another embodiment, an essentially non-cytolytic retrovirus is also avirulent, preferably through deletion of the nef gene. Accordingly, the present invention provides a vaccine comprising an avirulent, essentially non-cytolytic retrovirus comprising a nucleic acid sequence addition or deletion that renders the virus avirulent and wherein the natural signal sequence of the virus' envelope glycoprotein is either modified or replaced to provide an essentially non-cytolytic signal sequence.

Alternatively, the vaccine may comprise an effective amount of an avirulent and essentially non-cytolytic retrovirus wherein the natural signal sequence of the virus' envelope glycoprotein gp120 is modified to reduce the number of positive amino acids to no more than one positively charged amino acids, preferably no more than zero positively charged amino acids and the virus is rendered avirulent by deleting a sufficient portion of the nef gene.

Accordingly, the present invention also includes a method of preventing or treating a retroviral infection comprising administering a vaccine of the present invention to an animal in need thereof. As used herein, "vaccine" includes all prophylactic and therapeutic vaccines. According to one embodiment the vaccine contains an avirulent and essentially non-cytolytic recombinant retrovirus, wherein the NSS of the virus' envelope glycoprotein is modified to provide an essentially non- cytolytic NSS or is replaced with an essentially non-cytolytic NSS and the virus is rendered avirulent by deleting a sufficient portion of the nef gene.

The vaccine compositions of the invention are suitable for administration to subjects in a biologically compatible form in vivo. The expression "biologically compatible form suitable for administration in vivo" as used herein means a form of the substance to be administered in which any toxic effects are outweighed by the therapeutic effects. The substances may be administered to any animal, preferably humans.

The vaccines of the present invention may additionally contain suitable diluents, adjuvants and/or carriers. Preferably, the vaccines contain an adjuvant which can enhance the immunogenicity of the vaccine in vivo. The adjuvant may be selected from many known adjuvants in the art including the lipid-A portion of gram negative bacteria endotoxin, trehalose dimycolate of mycobacteria, the phospholipid lysolecithin, dimethyldictadecyl ammonium bromide (DDA), certain linear polyoxypropylene-polyoxyethylene (POP-POE) block polymers, aluminum hydroxide, and liposomes. The vaccines may also include cytokines that are known to enhance the immune response including GM-CSF, IL-2, IL-12, TNF and IFNγ.

The dose of the vaccine may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances.

The vaccines may be administered in a convenient manner such as by injection (subcutaneous, intravenous, intramuscular, etc.), oral administration, inhalation, transdermal administration (such as topical cream or ointment, etc.), or suppository applications.

Prevention of Apoptosis

The present invention also includes a method of preventing the NSS of a retrovirus from exerting its apoptotic effects on a cell, apoptosis induced by a retroviral infection. Accordingly, the present invention provides a method of preventing or inhibiting apoptosis comprising administering a sufficient amount of antagonist to NSS to an animal in need thereof. The antagonist may be any substance that can inhibit the NSS gene or its protein product referred to herein as "NSS protein", preferably the antagonist is an antibody or antisense molecule.

In one embodiment, the antagonist is a substance that inhibits the NSS protein such as an NSS protein specific antibody. Antibodies to NSS protein may be prepared using techniques known in the art such as those described by Kohler and Milstein, Nature 256, 495 (1975) and in U.S. Pat. No. RE 32,011, U.S. Pat. Nos. 4,902,614, 4,543,439, and 4,411,993 which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present invention, antibodies are understood to include monoclonal antibodies, polyclonal antibodies, antibody fragments (e.g., Fab, and F(ab')$_2$) and recombinantly produced binding partners. Consequently, the present invention provides a method of inhibiting the effects of the NSS of a retrovirus comprising administering an effective amount of an antibody that inhibits the NSS protein.

In addition to antibodies, other antagonists or ligands that bind to the NSS protein and inhibit its function may also be used. NSS protein ligands may be identified by assaying a sample for peptides that bind to NSS protein. Any assay system or testing method that detects protein-protein interactions may be used including co-immunoprecipitation, crosslinking and co-purification through gradients or chromatographic columns may be used. Biological samples and commercially available libraries may be tested for NSS protein-binding peptides. For example, labelled NSS protein or soluble NSS protein may be used to probe phage display libraries. In addition, antibodies that bind to NSS protein may be used to isolate other peptides with NSS protein binding affinity. For example, labelled antibodies may be used to probe phage display libraries or biological samples. Additionally, a nucleic acid sequence encoding a NSS protein may be used to probe biological samples or libraries for nucleic acids that encode NSS protein-binding proteins or ligands.

In another embodiment, the NSS antagonist is an antisense oligonucleotide that inhibits the expression of NSS protein. Antisense oligonucleotides that are complimentary to a nucleic acid sequence from an NSS protein gene can be used in the methods of the present invention to inhibit NSS protein.

Consequently, the present invention provides a method of inhibiting the effects of the NSS of a retrovirus comprising administering an effective amount of an antisense oligonucleotide that is complimentary to a nucleic acid sequence from an NSS protein gene to an animal in need thereof. Preferably the retrovirus is HIV-1.

The term antisense oligonucleotide as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucletide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

Furthermore, the present invention also contemplates a method for assaying for a substance that inhibits the NSS activity of a retrovirus comprising reacting a retrovirus containing an NSS with a test substance, under conditions which permit inhibition of the NSS, assaying for the ability of the retrovirus to induce apoptosis, and comparing to the ability to induce apoptosis obtained in the absence of the test substance, to determine the effect of the substance on the NSS of the retrovirus.

Apoptosis in Cancer Cells

The present invention further includes a method of killing or destroying target cells, preferably cancer cells, comprising administering to the cell or cells, an effective amount of a recombinant virus, preferably VSV or any other carrier RNA virus, specific for the target cells, containing, preferably the NSS of HIV-1. Preferably the cells are in an animal in need thereof, most preferably in human. Cells which are infected or cancerous, express cell specific markers for which a complementary recognition site may be incorporated into a suitable vector into which the NSS of HIV-1 has been incorporated. This approach has been taken with vesicular stomatitis virus (VSV) which has been engineered to incorporate the genes for CD4 and CXCR4 thereby targeting the modified VSV to infect HIV-1 infected cells (Schnell, M. J. et al. Cell 90: 849–857 (1997)). Accordingly, the present invention provides a method of killing target cells, such as cancer cells, comprising administering a recombinant virus containing NSS and a recognition site specific to the target cells, to an animal in need thereof. In an embodiment, the NSS of HIV-1 is incorporated into a modified VSV-like vector which has been targeted to a specific cancer cell type based on a particular cancer cell surface antigen thereby providing the VSV with the ability to induce apoptosis in the targeted cancer cells.

The following non-limiting examples are illustrative of the present invention:

EXAMPLES

Example 1

Construction of Recombinant Baculoviruses

Construction of recombinant baculoviruses expressing HIV-1 gp120-NSS, gp120-MSS, and gp120-ΔS has been described previously by Li et al. (Virology 204:266–278, 1994).

Construction of recombinant baculovirus expressing $VSV_{Ind}$ glycoprotein (G) was described previously by Bailey et al. (Virology 169:323–331, 1989).

Construction of recombinant baculovirus expressing $VSV_{Ind}$ G protein with HIV-1 env signal sequence (VSV-G-NSS):

To replace the signal sequence of VSV-G protein, the present inventors first constructed VSV-G-ΔS by PCR with two primers:

```
primer #1:   5'-GGC GGATCC GGATCA ACG TTC ACC ATA GTT-3'    (SEQ. ID. NO.:1)
(5' primer)          BamHI   SphI   +1VSV-G primer #2:   complementary to C-terminus gene of VSV-G
(3' primer) 5'GGC GGATCC TTA CTT TCC AAG TCG-3'              (SEQ. ID. NO.:2)
                   BamHI  stop codon
```

The plasmid pwK1 (which contains $VSV_{Ind}$ full-length G gene, and provided kindly by Dr. Robert R. Wagner, University of Virginia, U.S.A.) was used as the template, and amplified with the Gene amp kit by 30 cycles of PCR in a Perkin-Elmer Cetus Thermocycler (the cycles were 94° C., 1 min; 45° C., 2 min; 72° C., 3 min) from 20 ng of pwK1 as the template and 1.0 μM of each primer.

All primers had BamHI sites at their 5' terminus so that the amplified VSV-G-ΔS DNA fragment could be inserted into BamHI site of the plasmid, pbluescript SK VECTOR (Stratagene). The clone in which 5' terminus of VSV-G-ΔS toward T7 promoter was selected, and digested with SphI plus XhoI restriction enzymes. The vector is shown in FIG. 5.

Amplification of HIV-1 Signal Sequence:

The HIV-1 signal sequence of env gene was amplified from pBluescript-gp120-NSS by PCR with the following two primers:

```
primer #1         5'-AAT ACG ACT CAC TAT-3'         (SEQ. ID. NO.:3)
(T7 primer)

primer #2         5'-GGC GCATGC ACT ACA GAT CAT-3'  (SEQ. ID. NO.:4)
(complementary           SphI
to c-terminus
of HIV-1 signal
sequence gene)
```

This is illustrated in FIG. 6. The amplified DNA fragment containing HIV-1 signal sequence was digested with XhoI plus SphI restriction enzymes, and inserted into XhoI and SphI digested vector, pBluescript VSV-G-Δs. The resulting plasmid is designated as pBSK VSV-G-NSS, and the construct was further confirmed by DNA sequencing. This is illustrated in FIG. 7.

The BamHI fragment of VSV-G-NSS was inserted into the BamHI site of a baculovirus pAcYM1 (Li et al. Virology 204:266–278, 1994), and recombinant baculovirus expressing VSV-G-NSS was generated by standard transfection method (Li et al. Virology 204: 266–278, 1994).

Example 2

Microscopic Examination of Recombinant Baculoviruses Infected Cells

SF21 cells were infected with recombinant AcNPV at a m.o.i. of 5 PFU/cell and incubated at 27° C. for 48 hrs. The infected cells were examined by phase-contrast microscope. The results are shown in FIG. 1. (A) wild-type AcNPV-infected cells; (B) vAcgp120-NS-infected cells (rgp120 with the HIV-1 natural signal sequence showing cell lysis); (C) vAcgp120-ΔS-infected cells; (rgp120 without the signal sequence showing intact cells); (D) vAc8gp120-MS-infected cells (rgp120 with mellitin signal sequence showing intact cells); (E) vAcVSV-G-infected cells (VSV G protein showing intact cells); (F) vAcVSV-G-NS-infected cells. (VSV G protein with the HIV-1 env natural signal sequence showing cell lysis).

The above results demonstrate that the HIV-1 env signal sequence kills cells rapidly.

Example 3

Effects of the HIV-1 env Signal Sequence on Cell Death

Trypan Blue Assay:

SF21 cells were infected with recombinant AcNPV at an m.o.i. of 5 PFU/Cell for 1 hr, and the inoculum was removed and incubated with the complete medium TNM-FH containing 10% fetal bovine serum (FBS). At 24, 48, and 72 hrs after infection, cells were stained with trypan blue (GIBCO, BRL) for 5 min. and the cells were counted through the microscope and the percent of dead cells was determined by using the following formulae:

$$\frac{\text{Dead cells (stained)}}{\text{viable cells (unstained)} + \text{Dead cells}} \times 100 = \%\ \text{Dead Cells}$$

Lactate Dehydrogenase Release Assay (LDRA):

The LDRA was performed according to the instructions of the manufacturer (Boehringer Mannheim Cytotoxicity Detection Kit).

SF21 cells were infected with recombinant AcNPV at an m.o.i. of 5 PFU/cell for 1 hr. and the inoculum was removed and incubated with complete medium at 27° C., culture medium was collected at regular intervals of 12 hr. and centrifuged at 12,000 rpm for 1 min. The culture supernatant was diluted 10 fold and 100 μl of the supernatant was incubated with 100 μl of reaction mixture (cytotoxicity detection kit) for 30 min at room temperature. The absorbance of samples was measured at 490 nm by quantitating the formazen dye formed by using a microplate (ELISA) reader (Bio-Rad 550).

The results of the trypan blue and lactate dehydrogenase release assays are illustrated in FIGS. 2A and 2B, respectively. FIG. 2A; percentage of cells permeablized by trypan blue (dead cells) after expressing rgp120 or VSV-G proteins with different signal sequences. FIG. 2B; Lactate dehydrogenese (LDH) release assay. (Boehringer Mannheim's Cytotoxicity Detection Kit). The amounts of LDH released from SF21 cells infected with recombinant viruses expressing rgp120 or VSV-G with different signal sequences were measured by quantitating the formazan dye formed in ELISA plates read at 490 nm.

In conclusion rgp120 and VSV-G with the HIV-1 env natural signal sequence kill cells much faster. Cells survive much longer without the HIV-1 env natural signal sequence or with mellitin signal sequence. The HIV-1 env natural signal sequence is responsible for rapid cell death.

Example 4

Figure 3:
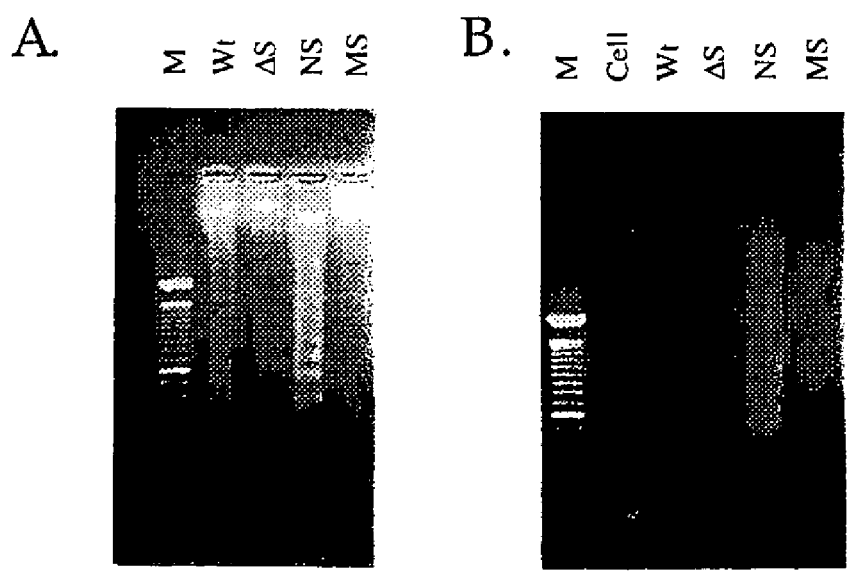
FIG. 3 shows agarose gel electrophoresis results providing an analysis of DNA fragmentation of SF21 cells infected with recombinant AcNPV expressing gp120 with different signal sequences.

Examination of Apoptosis:

Total DNA Extraction Method:

SF21 cells ($3\times10^6$) were infected with recombinant AcNPV at an m.o.i. of 5 PFU/cell for 1 hr. The inoculum was removed and incubated with complete medium at 27° C. for 48 hr. Cells were pelleted at 2500 rpm for 10 min and extracted with TSE (10 mM Tris, pH 8.0, 1 mM EDTA, 1% SDS, to which proteinase K to a final concentration of 70 µg/ml was added). Then, samples were incubated for 2 hr at 37° C., and at the end of incubation NaCl was added to a final concentration of 1M and then samples were incubated at 4° C. overnight. The DNA was extracted with phenol:chloroform (1:1) and with chloroform. Finally ethanol (100%) was added to precipitate the DNA (15 min at 80° C.) and the DNA precipitate was pelleted by micro-centrifugation at 12,000 rpm for 15 min. The DNA pellet was washed once with 70% ethanol. resuspended in TE (10 mM Tris, pH 8.0, 1 mM EDTA) with RNase A (50 µg/ml), electrophoresed on 1.2% agarose gel and stained with ethiolium bromide. (N. Chejanovsky and E. Gershburg, Virology 209: 519–525, 1995). The results are illustrated in FIG. 3. Total cellular DNA (A) or low molecular weight DNA (B) was extracted at 48 hr. post infection and analyzed by 1.2% agarose gel electrophoresis in the presence of ethiolium bromide. Lanes M, DNA marker; Lanes WT, wild-type AcNPV-infected cells; Lanes AS-infected cells (rgp120 without the signal sequence); Lane NSS, vAcgp120-NS-infected cells (rgp120 with the HIV-1 env natural signal sequence); Lanes MSS, vAcgp120-MS-infected cells (rgp120 with mellitin signal sequence). The above results demonstrate that the HIV-1 env natural signal sequence induces apoptosis.

Extraction of Fragmented DNA:

SF21 cells were infected with vAcVSV-G (VSV-G) or vAcVSV-G-NSS (VSV-G-NSS) at a m.o.i. of 5 PFU/cell and incubated at 27° C. for 48 hours. At 48 hr. postinfection, SF21 cells ($3\times10^6$) were pelleted at 2500 rpm for 5 min and lysed in solution containing 10 mM Tris HCl (pH 8,0), 10 mM EDTA, and 0.5% Triton X-100, and centrifuged at 12,000 rpm for 25 min in an Eppendorf microcentrifuge to pellet chromosome DNA. The supernatant was digested with 0.1 mg of RNaseA per ml at 37° C. for 1 hr and then for 2 hr with 1 mg proteinase K per ml at 50° C. in the presence of 1% SDS, extracted with phenol and chloroform, precipitated with cold ethanol. The precipitate was resuspended in TE and subjected to electrophoresis on 11.5% agarose gel containing 5 µg of ethidium bromide per ml. DNA was visualized by UV transillumination. (Rosario Leopardi and Bernard Roizman, Proc. Natl. Acad. Sci. USA 93:9583–9587, 1996).

Figure 4:
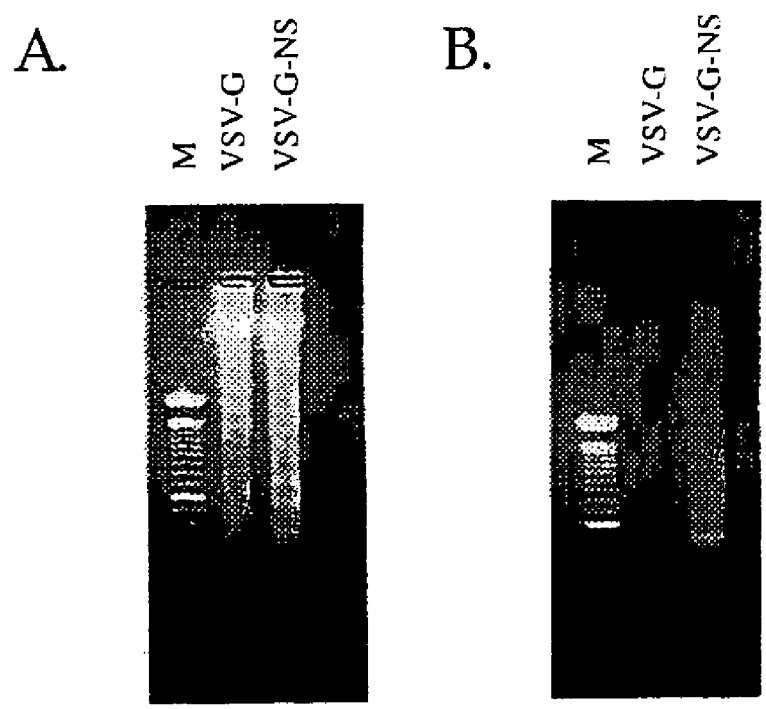
FIG. 4 shows agarose gel electrophoresis providing an analysis of DNA fragmentation of SF21 cells infected with recombinant baculovirus expressing vesicular stomatitis virus glycoprotein G (VSV-G) with or without the HIV-1 env natural signal sequence.
Figure 5:
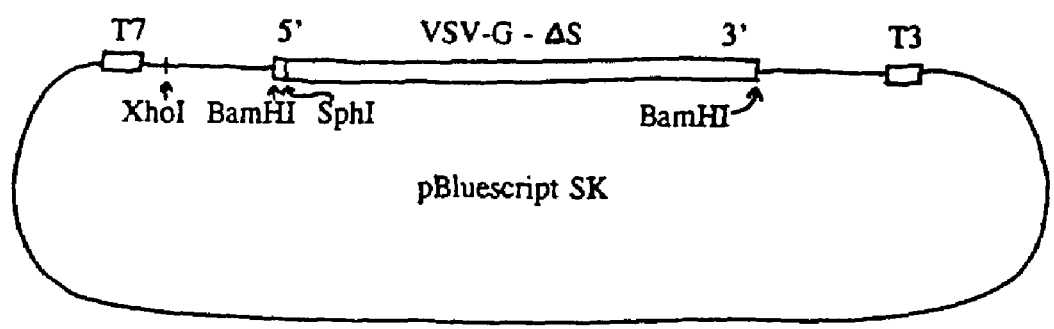
FIG. 5 is an illustration of a recombinant plasmid construction of VSV-G protein without signal sequence.
Figure 6:
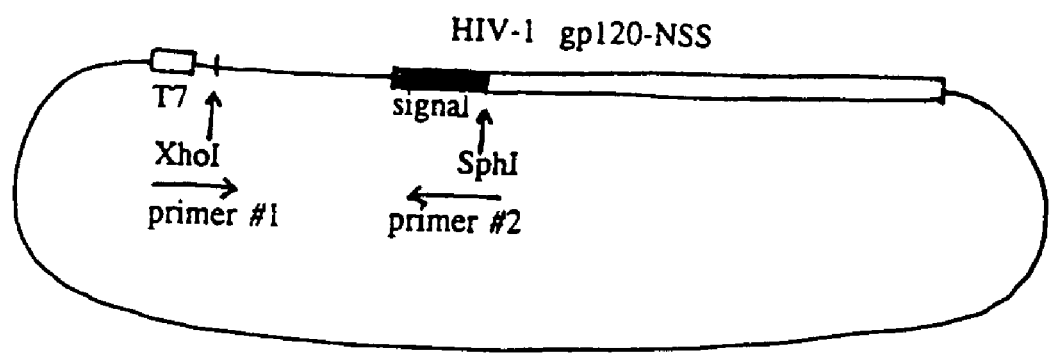
FIG. 6 is an illustration of a construction of HIV-1 gp120 containing the NSS.
Figure 7:
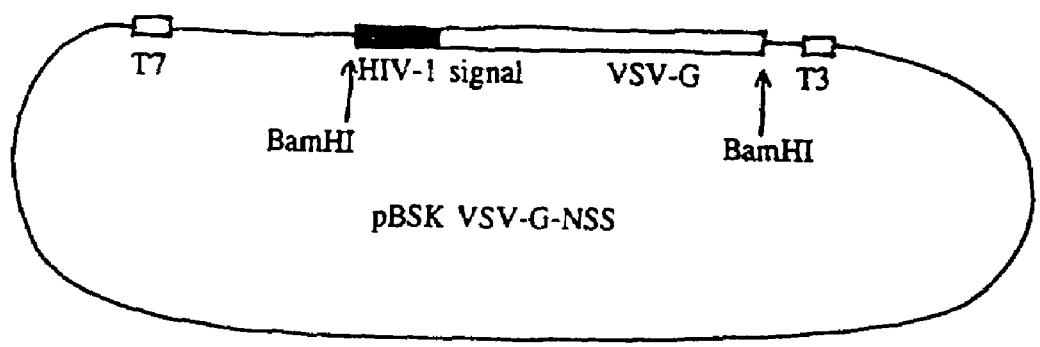
FIG. 7 is an illustration of plasmid pBSK VSV-G-NSS; this plasmid contains VSV-G protein gene sequence with the natural signal sequence of the HIV-1 env protein.
Figure 8:
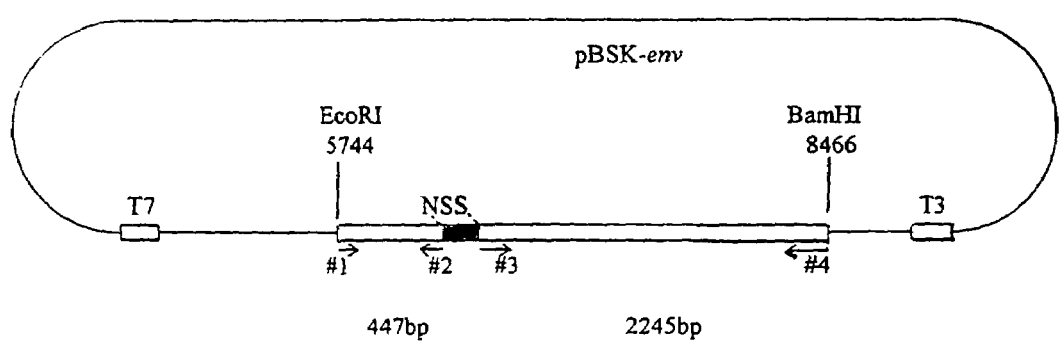
FIG. 8 is an illustration of a recombinant plasmid construction where the EcoRI-BamHI site contains the subcloned fragment of pNL4-3 in pbluescript SK vector.
Figure 9:
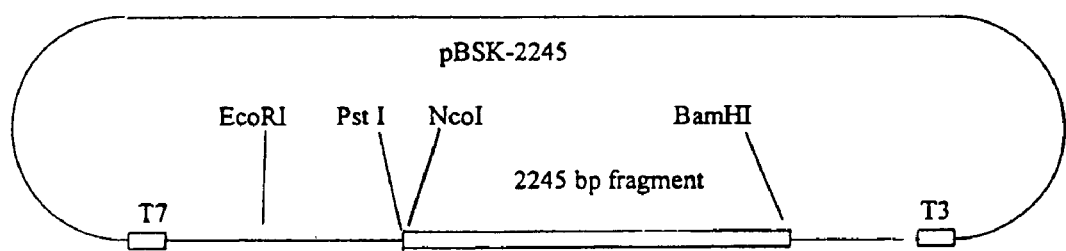
FIG. 9 is an illustration of a recombinant plasmid construction containing a 2245 bp fragment cloned into the PstI+BamHI sites.
Figure 10:
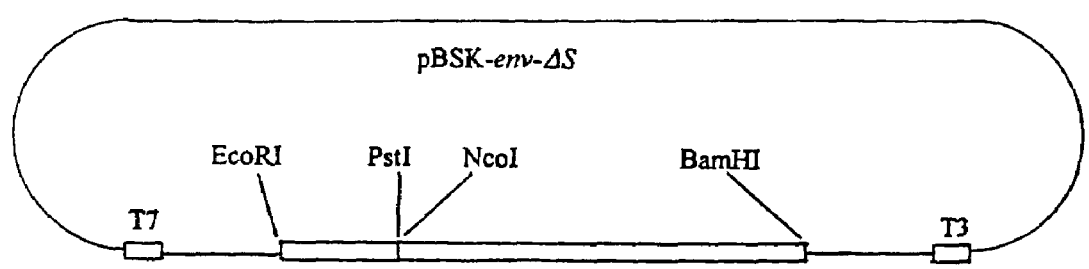
FIG. 10 is an illustration of a recombinant plasmid construction containing EcoRI and Pst-I digested PCR products (445 bp fragment).

The results are shown in FIG. 3, Panel B and FIG. 4, Panel B.

Example 5

Construction of Recombinant HIV-1 Containing Partial vpu and nef deletion and NSS Substitution 1. Construction of Plasmid pNL4-3 Containing the NSS Substitution (with MSS, IL-3 or Any Other Signal Sequences) and vpu Deletion.

An infectious HIV-1 proviral DNA clone, pNL4-3 (provided by Dr. Malcolm Martin through the AIDS Research and Reference Reagent program, Division of AIDS, NIAID, NIH, Adachi et al, J. Virol. 59:284–291, 1986), contains two unique restriction enzyme sites; EcoRI (position 5744) and BamHI (position 8466). The env gene encoding region starts from position 6221 and ends at position 8785. To replace the natural signal sequence of HIV-1 env with mellitin, IL-3 or any other secretory protein signal sequences, the EcoRI–BamHI fragment of pNL4-3, is isolated from agarose gel, and subcloned into the EcoRI–BamHI site of pBluescript SK vector as illustrated in FIG. 8. From this product, four primers are designed as follows:

```
primer #1 (Forward):
5'-GGC GAATTC TGC AAC AAC TGC TG-3'                         (SEQ. ID. NO.:5)
        EcoRI primer #2 (Reverse):
5'-GGC CTG CAG TCA TTA GGC ACT GTC TTC TGC TCT TTC-3'       (SEQ. ID. NO.:6)
         PstI  Stop codons primer #3 (Forward):
5'-GGC CTGCAG CCATGG ACA GAA AAA TTG TTG GTC ACA GTC-3'     (SEQ. ID. NO.:7)
        PstI   NcoI primer #4 (Reverse):
5'-GGC GGATCC GTT CAC TAA TCG AAT GG-3'                     (SEQ. ID. NO.:8)
       BamHI
```

The pBSK-env as template plus primers #1 and #2 are used and PCR is performed to amplify the left portion of env region, 477 bp fragment. Similarly, primers #3 and #4 are employed to amplify the right portion of env, 2245 bp. The EcoRI–PstI PCR product (477 bp fragment) was digested with EcoRI+PstI whereas the PstI–BamHI PCR product (2245 bp fragment) was cut with PstI+BamHI. Then, the PstI-BamHI digested 2245 bp fragment was cloned into the PstI+BamHI sites of pBSK vector as shown in FIG. 9.

Following this, the pBSK-2245 was digested with EcoRI+PstI and ligated with the EcoRI+PstI digested PCR products (445 bp fragment) resulting in the plasmid pBSK-env-ΔS, as shown in FIG. 10.

The plasmid pBSK-env-ΔS was digested with PstI+NcoI and then ligated with the synthetic oligonucleotide encoding MSS, IL-3 signal sequences or any other desired signal sequences. This synthetic oligonucleotide contains a PstI site at 5' end and a NcoI site at 3' end. Before ligation into the vector, these double strand oligonucleotides were first digested with PstI+NcoI.

A. Synthetic Olignonucleotide Encoding Mellitin Signal Sequence (Only the Positive Sense is Shown):

```
        PstI
5'-GGC CTG CAG ATG AAA TTC TTA GTC AAC GTT GCC      (SEQ. ID. NO.:9)

CTT GTT TTT ATG GTC GTG TAC ATT TCT TAC

ATC TAT GCG GAT CCA TGG GCC-3'
                   NcoI
```

Synthetic oligonucleotide encoding interleukin-3 signal sequence: (only the positive sense is shown):

```
        PstI
5'-GGC CTG CAG ATG CTG CTC CTG CTC CTG ATG CTC      (SEQ. ID. NO.10)

TTC CAC GGA CTC CAA GCT TCA ATC AGT GGC GAT

CCATGG  GCC-3'
    NcoI
```

Figure 11:
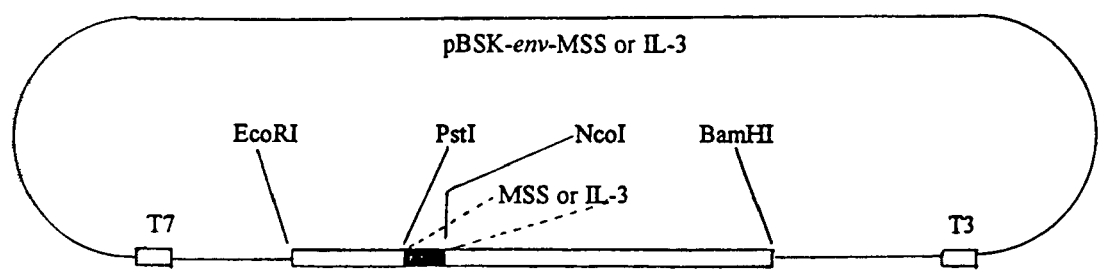
FIG. 11 is an illustration of a recombinant plasmid construction containing an oligonucleotide encoding either mellitin signal sequence or interleukin-3 signal sequence.

The resulting recombinant plasmid is shown in FIG. 11.

After sequencing to verify the correct modification, the plasmid was digested with EcoRI+BamHI to isolate the EcoRI–BamHI fragment, which was recloned into the EcoRI–BamHI sites of pNL4-3 proviral DNA vector. The resulting plasmid is designated pHIV-1-MSS (or pHIV-1-IL3SS).).

In addition, during the above construction, the NSS is substituted with not only MSS or Il-3 signal sequence, but also created partial vpu gene deletion. The vpu encodes 82aa and its 3' end overlaps with the signal sequence of HIV-1 env gene, about 28aa. However, it is in a different reading frame (−1 reading frame). Studies have shown that the deletion of vpu or nef genes did not alter the virus replication in either chimpanzee PBMCs, human PBMCs, or in the B/T cell hybrid line CEMx174 (James et al, AIDS Res. Human Retrovirus 10:343–350, 1994). Therefore, during the PCR amplification of 455 bp-fragment of the left portion of env with primers #1 and #2, two stop codons were added just in front of the start codon of env genes which results in the deletion of 28aa of vpu (see primer #2).

2. Construction of Plasmid Containing nef Deletion.

Figure 12:
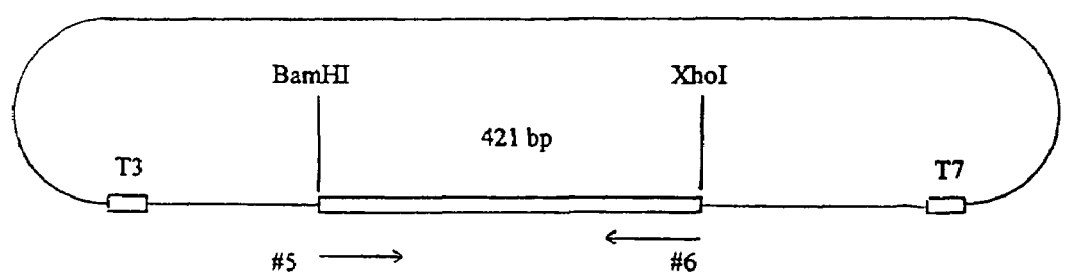
FIG. 12 is an illustration of a recombinant plasmid construction containing a 421 bp fragment isolated from the nef gene coding sequence in the Bam HI-XhoI sites of the vector.

The nef gene coding sequence starts from position 8787 and ends at position 9407 in pNL4-3 proviral DNA clone. There are also two unique restriction enzyme sites; BamHI site at position 8466 in env gene and XhoI site at position 8887 in nef gene. To make the nef gene deletion, the plasmid HIV-1 MSS (or IL-3SS) was digested with BamHI and XhoI. The resulting 421 bp of BamHI–XhoI fragment was isolated and subcloned into the BamHI–XhoI sites of pBSK vector as shown in FIG. 12.

Two primers were designed:

```
Primer #5:          BamHI
(Forward)   5'-GGC GGATCC TTA GCA CTT ATC TGG-3'       (SEQ. ID. NO.:11)

XhoI
```

-continued

```
Primer #6:  5'-GCC CTC GAG TCA TTA ATA CTG CTC CCA CCC-3'  (SEQ. ID. NO.:12)
                               Stop codons
```

The nef gene encodes 260aa according to the present design. Two stop codons were inserted at the XhoI site which results in the nef only coding 33aa. After PCR amplification and BamHI+XhoI digestion, this 421 bp of PCR DNA fragment was cloned back into the BamHI–XhoI pHIV-1-MSS (or IL-3SS) vector. The resulting recombinant plasmid contains the NSS substitution and partial vpu and nef deletion, which is used for the vaccine test.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A recombinant human immunodeficiency virus-1 (HIV-1), wherein the natural signal sequence (NSS) of the HIV-1 envelope glycoprotein gp120 of the virus is replaced with a signal sequence selected from the group consisting of mellitin signal sequence (MSS) and interleukin 3 signal sequence (ILSS).

2. The HIV-1 of claim 1 wherein the retrovirus is avirulent.

3. The HIV-1 of claim 2 wherein the retrovirus is rendered avirulent by deletion of the nef gene.

4. The HIV-1 of claim 1 wherein the MSS is shown as SEQ ID NO 9.

5. The HIV-1 of claim 1 wherein the ILSS is shown as SEQ ID NO 10.

6. The HIV-1 of claim 4 wherein the retrovirus is avirulent.

7. The HIV-1 of claim 5 wherein the retrovirus is avirulent.

8. The HIV-1 of claim 6 wherein the retrovirus is rendered avirulent by deletion of the nef gene.

9. The HIV-1 of claim 6 wherein the retrovirus is rendered avirulent by deletion of the nef gene.

10. A immunogenic composition comprising an effective amount of the HIV-1 of claim 6.

11. An immunogenic composition comprising an effective amount of the HIV-1 of claim 7.

12. An immunogenic composition comprising an effective amount of the HIV-1 of claim 8.

13. An immunogenic composition comprising an effective amount of the HIV-1 of claim 9.

* * * * *

SEQUENCE LISTING

<160> NUMBER OF SEQ ID NOS: 12

<210> SEQ ID NO 1
<211> LENGTH: 30
<212> TYPE: DNA
<213> ORGANISM: Artificial Sequence
<220> FEATURE:
<223> OTHER INFORMATION: Vesicular stomatitis virus

<400> SEQUENCE: 1
ggcggatccg gatcaacgtt caccatagtt 30

<210> SEQ ID NO 2
<211> LENGTH: 24
<212> TYPE: DNA
<213> ORGANISM: Artificial Sequence
<220> FEATURE:
<223> OTHER INFORMATION: Vesicular stomatitis virus

<400> SEQUENCE: 2
ggcggatcct tactttccaa gtcg 24

<210> SEQ ID NO 3
<211> LENGTH: 15
<212> TYPE: DNA
<213> ORGANISM: Artificial Sequence
<220> FEATURE:
<223> OTHER INFORMATION: Human immunodeficiency virus type 1

<400> SEQUENCE: 3
aatacgactc actat 15

<210> SEQ ID NO 4
<211> LENGTH: 21
<212> TYPE: DNA
<213> ORGANISM: Artificial Sequence
<220> FEATURE:
<223> OTHER INFORMATION: Human immunodeficiency virus type 1

<400> SEQUENCE: 4
ggcgcatgca ctacagatca t 21

<210> SEQ ID NO 5
<211> LENGTH: 23
<212> TYPE: DNA
<213> ORGANISM: Artificial Sequence
<220> FEATURE:
<223> OTHER INFORMATION: Human immunodeficiency virus type 1

-continued

```
<400> SEQUENCE: 5
ggcgaattct gcaacaactg ctg                                              23

<210> SEQ ID NO 6
<211> LENGTH: 36
<212> TYPE: DNA
<213> ORGANISM: Artificial Sequence
<220> FEATURE:
<223> OTHER INFORMATION: Human immunodeficiency virus type 1

<400> SEQUENCE: 6
ggcctgcagt cattaggcac tgtcttctgc tctttc                                36

<210> SEQ ID NO 7
<211> LENGTH: 39
<212> TYPE: DNA
<213> ORGANISM: Artificial Sequence
<220> FEATURE:
<223> OTHER INFORMATION: Human immunodeficiency virus type 1

<400> SEQUENCE: 7
ggcctgcagc catggacaga aaaattgttg gtcacagtc                             39

<210> SEQ ID NO 8
<211> LENGTH: 26
<212> TYPE: DNA
<213> ORGANISM: Artificial Sequence
<220> FEATURE:
<223> OTHER INFORMATION: Human immunodeficiency virus type 1

<400> SEQUENCE: 8
ggcggatccg ttcactaatc gaatgg                                           26

<210> SEQ ID NO 9
<211> LENGTH: 84
<212> TYPE: DNA
<213> ORGANISM: Artificial Sequence
<220> FEATURE:
<223> OTHER INFORMATION: Apis mellifera

<400> SEQUENCE: 9
ggcctgcaga tgaaattctt agtcaacgtt gcccttgttt ttatggtcgt gtacatttct      60
tacatctatg cggatccatg ggcc                                             84

<210> SEQ ID NO 10
<211> LENGTH: 75
<212> TYPE: DNA
<213> ORGANISM: Artificial Sequence
<220> FEATURE:
<223> OTHER INFORMATION: Interleukin - 3

<400> SEQUENCE: 10
ggcctgcaga tgctgctcct gctcctgatg ctcttccacg gactccaagc ttcaatcagt      60
ggcgatccat gggcc                                                       75

<210> SEQ ID NO 11
<211> LENGTH: 24
<212> TYPE: DNA
<213> ORGANISM: Artificial Sequence
<220> FEATURE:
<223> OTHER INFORMATION: Human immunodeficiency virus type 1

<400> SEQUENCE: 11
```

-continued

```
ggcggatcct tagcacttat ctgg                              24

<210> SEQ ID NO 12
<211> LENGTH: 30
<212> TYPE: DNA
<213> ORGANISM: Artificial Sequence
<220> FEATURE:
<223> OTHER INFORMATION: Human immunodeficiency virus type 1

<400> SEQUENCE: 12
gccctcgagt cattaatact gctcccaccc                        30
```